United States Patent [19]

Lee et al.

[11] Patent Number: 4,863,539
[45] Date of Patent: Sep. 5, 1989

[54] HAPTIC ATTACHMENT FOR INTRAOCULAR LENSES

[75] Inventors: Wendell Lee, Banning; Miguel J. Leon, Whittier, both of Calif.

[73] Assignee: Optical Radiation Corporation, Azusa, Calif.

[21] Appl. No.: 118,219

[22] Filed: Nov. 6, 1987

[51] Int. Cl.$^4$ .................. B32B 31/02; B32B 31/14; A61F 2/16

[52] U.S. Cl. .................. 156/83; 156/91; 156/275.5; 156/293; 623/6; 264/1.7

[58] Field of Search .................. 623/6; 264/1.1, 1.7; 29/522 R; 156/83, 91, 275.5, 293

[56] References Cited

U.S. PATENT DOCUMENTS 4,668,446 5/1987 Kaplan et al. .................. 623/6 X
4,731,079 3/1988 Stoy .................. 623/6

FOREIGN PATENT DOCUMENTS 0208546 1/1987 European Pat. Off. .................. 623/6

Primary Examiner—Ronald L. Frinks
Attorney, Agent, or Firm—Christie, Parker & Hale

[57] ABSTRACT

An intraocular lens comprises a semirigid optic and one or more rigid haptics securely attached to the optic. The optic comprises a peripheral bore and a transverse bore generally normal to the peripheral bore which intersects the peripheral bore. The inner end of a rigid filamentous haptic is disposed within the peripheral bore and a rigid pin is disposed within the transverse bore. The pin is fixedly attached to the haptic to form an anchor within the optic.

12 Claims, 1 Drawing Sheet

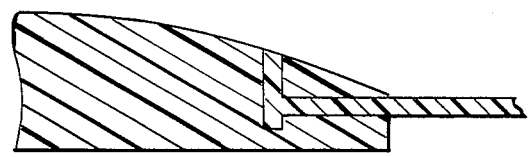
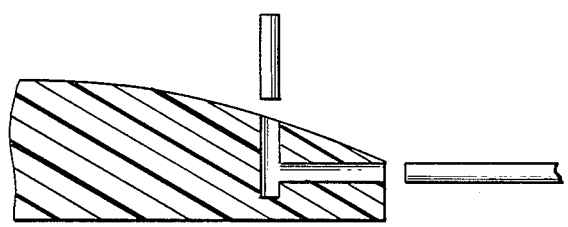
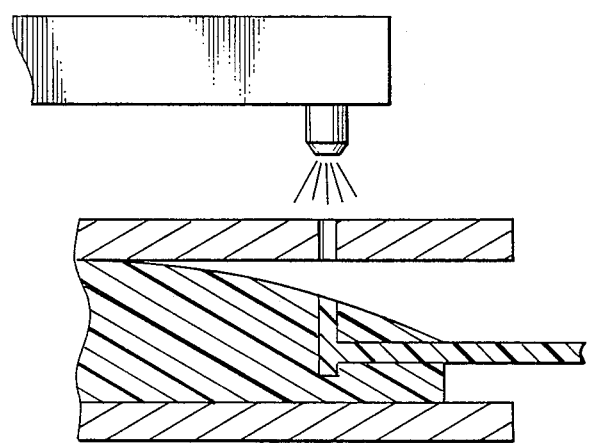

HAPTIC ATTACHMENT FOR INTRAOCULAR LENSES

FIELD OF THE INVENTION

This invention relates to an intraocular lens having a soft flexible optic and one or more rigid haptics and to a method for attaching rigid haptics to a soft flexible optic.

BACKGROUND OF THE INVENTION

The replacement of a natural lens with an artificial intraocular lens implant in the human eye has become a well known procedure to physicians specializing in ophthalmology. In such a procedure, a cornea-scleral incision is made in the eye through which the natural lens is removed and the artificial intraocular lens is inserted. The intraocular lens may be designed to be positioned within either the interior or posterior chamber of the eye.

Intraocular lenses typically include a central lens section, referred to as the optic, for focusing the light onto the retina. One or more supporting structures, called haptics, extend outwardly from the optic to a line and stabilize the optic with respect to the pupil. Typically, the haptics comprise one or more filamentous or wire-like arms or loops which extend radially outwardly from the periphery of the optic. The haptics may be fixed in position within the eye by sutures or by engagement with predetermined eye tissues.

The optic of the intraocular lens may be made of a rigid material such as polymethylmethacrylate (PMMA) or a soft, flexible, semirigid material such hydrogels, silicones and the like. Filamentous haptics, on the other hand, are usually, if not always, made of rigid materials such as polypropylene, PMMA or the like. This is because semirigid materials tend to be too weak to support the optic within the eye.

Soft, flexible optics offer an advantage over rigid optics in that they can be inserted into the eye or through an incision of reduced size. Smaller incisions are desired to minimize trauma to the eye. For example, Mazzoco U.S. Pat. No. 4,573,998 describes a method for the intrusion of an intraocular lens through a small incision by deforming, e.g. folding, the intraocular lens. Schacher U.S. Pat. No. 4,373,218 describes an inflatable intraocular lens which can be inserted while in a deflated state through a small incision and then inflated once in position within the eye. Siepser U.S. Pat. No. 4,556,998 describes an intraocular lens made of a hydrogel material which is inserted into the eye in a dehydrated non-swollen state and allowed to swell to its final shape within the eye.

One of the problems in the manufacture of intraocular lens having a soft, flexible optic is in the attachment of the haptic to the optic. Conventional methods of haptic attachment such as heat staking do not provide a strong enough bond between the material of the optic and the material of haptic.

Kaplan et al. U.S. Pat. No. 4,668,446 discloses a method for attaching a rigid haptic to a nonrigid or semirigid optic. In this method, a peripheral bore is formed in the optic. The optic is then swollen in an organic fluid to enlarge the bore. A haptic having an enlarged end is then inserted into the bore and the organic fluid is then removed from the optic. This reduces the size of the bore which contracts around the enlarged section securing the haptic to the optic.

SUMMARY OF THE INVENTION

The present invention provides an intraocular lens having an optic of a semirigid material and one or more rigid filamentous haptics secured to the optic by a rigid pin in a "T-" or "L-shaped" anchor arrangement.

In a preferred embodiment of the invention, the intraocular lens comprises a semirigid optic having one or more peripheral bores which extend inwardly generally from the periphery of the optic. A transverse bore intersects the peripheral bore. The inner end of a filamentous haptic extends into each peripheral bore. A rigid pin preferably made of the same material as the haptic, extends through the transverse bore and is rigidly attached to the haptic.

The present invention further provides a method for attaching a rigid haptic to a semirigid optic. The method comprises forming in the optic a peripheral bore and a transverse bore wherein the transverse bore intersects the peripheral bore. The proximal end of a haptic is then inserted into the peripheral bore. A pin, e.g., a short rod or bar, of a rigid material compatible with the material of the haptic is then inserted into the transverse bore. The bar is then attached or bonded to the proximal end of the haptic to anchor the haptic to the optic.

In a preferred embodiment, the semirigid optic comprises a rigid dry state and is swellable in water to a semirigid state and can be further swelled in an organic fluid. In the embodiment, a peripheral bore and a transverse bore intersecting the peripheral bore are formed in the optic while the optic is in its dry state. The optic is then immersed in water wherein the optic swells to its hydrated state. The optic is then immersed in an organic liquid when the optic further swells.

The inner end of a rigid haptic is then inserted into the peripheral bore and a rigid pin is inserted into the transverse bore and into contact with the haptic. The construction thus formed is then removed from the organic liquid and reimmersed in water, wherein the intraocular lens contracts to thereby hold the haptic and the pin in place. The pin is then fixedly attached to the haptic to form an anchor within the optic.

BRIEF DESCRIPTION OF THE DRAWINGS

These and other features and advantages of the present invention will be better understood by reference to the following detailed description when considered in conjunction with the accompanying drawings wherein:

FIG. 1 is a cross-sectional view of a preferred intraocular lens constructed in accordance with the present invention;

FIG. 2 is an exploded cross-sectional view of the intraocular lens shown in FIG. 1; and FIG. 3 is a cross-sectional view of the intraocular lens of FIG. 1 shown in a fixture for fusing the pin to the haptic.

DETAILED DESCRIPTION

In accordance with the present invention, there is provided an intraocular lens suitable for implantation in the eye comprising a semirigid optic and one or more rigid haptics securely attached to the semirigid optic by means of a transversely extending rigid pin attached to the haptic.

As used herein, "semirigid" material refers to any medical grade material suitable for use in intraocular lenses which is soft and pliant in the environment of the eye. Such materials include hydrogel or hydrophilic materials, e.g., as disclosed in Banko U.S. Pat. No. 4,235,199 and Barrett U.S. Pat. No. 4,664,668; silicone materials, e.g., as disclosed in Dekhert et al. U.S. Pat. No. 4,153,641, Birdsall et al. U.S. Pat. No. 4,198,131 and Jardan et al. U.S. Pat. No. 4,206,518; "memory" materials, e.g., as disclosed in Mazzoco U.S. Pat. No. 4,573,988 and Stoy U.S. Pat. application Ser. No. 935,224, now U.S. Pat. No. 4,731,079; and acrylic-type polymers softened by esterification as described in Kaplan et al.; U.S. Pat. No. 4,668,446; all of which are incorporated herein by reference. It is understood that the above materials are merely illustrative of materials suitable for use in the present invention and that the present invention is not limited to with these specific materials.

While not required for the practice of the invention, it is preferred that the material of the optic comprise an ultraviolet absorber. Suitable ultraviolet absorbers are described, for example, in Posin U.S. Pat. No. 4,636,212, which is incorporated herein by reference.

As used herein, "rigid" materials reflects nonpliant materials suitable for use in intraocular lenses. Such rigid materials include polypropylene, polyacrylates and polymethacrylates, e.g., PMMA. If polyacrylates or polymethacrylates are used, it is preferred that they comprise sufficient cross-linking agents to increase the temperature resistance of the resulting polymer sufficiently to withstand autoclaving temperatures. It is preferred that the material of the haptics comprise a pigment to impart color to the haptics to facilitate manipulation of the haptics during placement of the intraocular lens in the eye.

With reference to FIGS. 1 and 2, there is shown a preferred intraocular lens 10 constructed in accordance with the present invention. The intraocular lens 10 comprises a pair of rigid haptics 11 secured to a semirigid optic 12 by means of a rigid pin 15 attached to the haptic 11 to thereby form an anchor within the optic 12.

The optic 12 comprises a pair of peripheral bores 13. The direction and location of the peripheral bores 13 is not critical. The peripheral bores 13 may lie generally in the plane of the optic 12 so that the haptics 11 also lie generally in the plane of the optic 12 or may be at a slight angle from the plane of the optic 12 as desired. The diameter of the peripheral bores 13 is not critical but is preferably selected to be about the same as the diameter of the haptics 11.

A transverse bore 14 extends inwardly from the front surface of the optic 12 and intersects each peripheral bore 13. It is understood that the transverse bore 14 may extend into optic 12 from the rear surface or may extend entirely through the optic. The transverse bore 14 is preferably generally normal to the peripheral bore 13, but may intersect the peripheral bore 13 at any desired angle.

In the embodiment shown, the transverse bore 14 extends past the peripheral bore 13. Alternatively, the transverse bore 14 may extend only to the peripheral bore 13 or, as mentioned above, may extend the entire thickness of the optic 12. It is preferred that the transverse bore 14 intersect the peripheral bore 13 at about the inner end of the peripheral bore 13, as shown. However, it is understood that the transverse bore 14 may intersect the peripheral bore 13 at any position along the length of the peripheral bore 13.

The diameter of the transverse bore 14, like the peripheral bore 13, is preferably selected to be about the same as the diameter of the pin 15.

In accordance with the method of the invention, the peripheral and transverse bores 13 and 14 are formed when the optic is in a rigid, e.g., dehydrated, state. The peripheral and transverse bores 13 and 14 may be formed by any conventional method such as drilling, cutting, coring, and the like.

Once the peripheral and transverse bores 13 and 14 have been formed, the optic 12 is immersed in water until fully hydrated. Immersion times from about 16 to about 24 hours are typically sufficient, depending on the material of the optic.

After the optic 12 has been hydrated, it is removed from the water and immersed in an organic liquid. The organic liquid further swells the optic which further increases the diameter of the peripheral and transverse bores 13 and 14 without attacking or otherwise detrimentally affecting the material of the optic 12. Preferred organic liquids include acetone, ethanol, methyl ethyl ketone, and the like. Mixtures may be used along with aqueous solutions comprising the organic liquid, if desired. Acetone is presently preferred.

Once the optic 12 has been further swollen by immersion in the organic liquid-containing solution, the optic 12 is removed and the inner end of the haptic 11 is inserted into the peripheral bore 13. The pin 15 having a length about the same as the depth of the transverse bore 14 is then inserted into the transverse bore 14. In this arrangement, the inner end of the haptic contacts the pin 15.

The organic liquid is then removed from construction thus formed. Any suitable technique may be used for removing the organic liquid. For example, the lens construction may be heated in an oven at a temperature and for a time sufficient to remove the organic liquid without damaging the lens construction. Once the organic liquid has been removed, the lens construction is reimmersed in water to rehydrate the optic. Alternatively, the lens construction may be simply immersed in water for time sufficient for the organic liquid to diffuse out of the optic.

Removal of the organic liquid reduces the swelling of the optic and causes the peripheral and transverse bores 13 and 14 to contract about the haptic 11 and pin 15, respectively. Contraction of the peripheral and transverse bores 13 and 14 holds the haptic 11 and pin 15 securely in the desired positions.

With reference to FIG. 3, the intraocular lens construction thus formed is then placed in a holding fixture 16 between a top plate 17 and a bottom plate 18. The plates 17 and 18 may be made of any material which is opaque to the light. The top plate 17 comprises a hole 19 which is aligned with the transverse bore 14 and pin 15 The hole 19 has a diameter about the same as the diameter of the transverse bore 14 and pin 15. Light from a photocoagulator 21 is directed through the hole 19 in the top plate 17 to thereby fuse the haptic 11 and pin 15 together. The top plate 17 prevents the light from damaging the optic 12. The above fusing procedure is then repeated with each of the other haptics 11.

It is understood that many variations of the above procedure can be practiced without departing from the scope of the present invention. For example, it is apparent that the number and/or locations of the transverse bores and hence the pins may vary as desired. Moreover, while it is preferred to form the transverse and peripheral bores when the optic is in a dry rigid state, the bores may be formed when the optic in its semirigid state, if desired.

It is preferred that the optic be swollen in an organic fluid after it has been hydrated. This facilitates insertion of the haptic and pin into the peripheral and transverse bores. However, the step of further swelling the optic in an organic fluid is understood to be optional. Rather, the haptic and pin may be inserted into the peripheral and transverse bores when the haptic is in its normal semirigid state. In such an embodiment, care must be taken to avoid damaging, e.g., tearing, the optic.

It is presently preferred to fixedly attach the pin to the haptic by fusing with light from a photocoagulator. However, it is understood that any suitable method for fixedly attaching the pin to the haptic may be used. For example, the pin may be fused to the haptic by the use of laser radiation focused on the pin. Alternatively, the pin may be bonded to the haptic by an adhesive or solvent. If the latter procedure is used, care must be exercised not to damage the material of the optic.

Depending on the materials of the optic and pin, the pin may be formed within the transverse bore and in contact with the inner end of the haptic to thereby bond to the haptic. In such an embodiment, a polymerized composition is injected into the transverse bore and allowed to polymerize therein. Such a procedure is not preferred because the monomers of the polymerizable composition of the pin tend to be a solvent for most suitable materials of the optic, and hence tend to damage the material of the optic.

EXAMPLE

An optic measuring 7.00 mm in diameter in its hydrated state and 6.69 mm in its dehydrated state made of a polymeric material comprising about 20% by weight methyl methacrylate, about 73.8% by weight hydroxyethyl methacrylate, about 1.2% by weight ethylene glycol dimethacrylate, about 5% by weight UV absorber and about 0.0375% by weight catalyst was provided. Two peripheral bores measuring about 0.10 to about 0.11 mm in diameter and about 2.00 mm in depth were made in the rigid optic in its rigid dehydrated state by means of a radial drill. Two transverse bores measuring about 0.30 to about, 0.35 mm in diameter and about 1.00 mm in depth were then made in the rigid optic by axial drill. The transverse bores intersected the inner ends of the peripheral bores.

The rigid optic was immersed in water for approximately 15 hours to thereby provide a swollen, hydrated optic. The hydrated optic was then immersed in an aqueous solution containing about 50% water and about 50% acetone for about 5 hours. The inner end of a 0.15 mm diameter haptic made of a filamentous polypropylene material sold by Ethicon, Inc. under the trademark PROLENE was then inserted into the peripheral bore and a pin, made of the same polypropylene material and having a diameter of 0.21 mm and a length of 1 mm, was inserted into the transverse bore.

The lens was then placed in a vacuum oven and subjected to a temperature of about 50° C. at a pressure of about 15psi for about 4 hours to remove the acetone. The lens was then immersed in deionized water for 4 hours to rehydrate the lens.

The lens was then placed in a holding fixture between a pair of metal plates. The upper plate had a hole about 0.50 mm in diameter which was aligned with one of the pins. The holding fixture was then placed in a photocoagulator sold by Optical Radiation Corporation under the trade designation PHOTOCOAGULATOR MODEL 514. The Xenon lamp of the photocoagulator was activated for about 30 seconds at a light intensity of 1000 watts to thereby fuse the pin to the haptic. The procedure is then repeated for the other haptic and pin.

What is claimed is:

1. A method for attaching a rigid haptic to an optic having a semirigid state in the environment of the eye comprising:
    forming a peripheral bore in the optic;
    forming a transverse bore in the optic, said transverse bore intersecting the peripheral bore;
    inserting the inner end of a rigid haptic into the peripheral bore;
    inserting a rigid pin into the transverse bore; and
    fixedly attaching the pin to the haptic to thereby securely attach the haptic to the optic.

2. A method as claimed in claim 1 wherein the optic has a rigid state and a semirigid state and the peripheral and transverse bores are formed when the optic is in its rigid state.

3. A method as claimed in claim 1 wherein the pin is fixedly attached to the haptic by fusing the pin to the haptic with a photocoagulator.

4. A method as claimed in claim 1 wherein the pin and haptic form a "T-shaped" anchor within the optic.

5. A method as claimed in claim 1 wherein the pin and haptic form an "L-shaped" anchor within the optic.

6. A method for attaching a rigid haptic to an optic having a rigid state in at least one first environment and a semirigid state in at least one second environment including the environment of the eye comprising:
    forming a peripheral bore and a transverse bore which intersects the peripheral bore in the optic when the optic is in its rigid state;
    placing the optic in a second environment wherein the optic becomes semirigid;
    inserting the inner end of a rigid haptic into the peripheral bore;
    inserting a rigid pin into the transverse bore; and
    fixedly attaching the pin to the haptic to thereby securely attach the haptic to the optic.

7. A method as claimed in claim 6 wherein the optic is dehydrated in its rigid state and hydrated in its semirigid state.

8. A method as claimed in claim 6 wherein the optic is rigid at a first temperature below the temperature within the eye and semirigid at the temperature of the eye.

9. A method for attaching a rigid haptic to an optic having a rigid dehydrated state, a swollen semirigid hydrated state and a further swollen state when immersed in an organic liquid comprising:
    forming a peripheral bore and a transverse bore which intersects the peripheral bore in the optic when the optic is in its rigid state;
    swelling the optic to its semirigid state by immersing the optic in water;
    further swelling the optic by immersing the optic in an organic liquid;
    inserting the inner end of a rigid haptic into the peripheral bore;
    inserting a rigid pin into the transverse bore; and
    fixedly attaching the pin to the haptic to thereby secure the haptic to the optic.

10. A method as claimed in claim 9 wherein the pin is fixedly attached to the haptic by fusing the pin to the haptic with a photocoagulator.

11. A method as claimed in claim 9 wherein the pin and haptic form a "T-shaped" anchor within the optic.

12. A method as claimed in claim 9 wherein the pin and haptic form an "L-shaped" anchor within the optic.

* * * * *